US007052686B2

(12) United States Patent
Lee et al.

(10) Patent No.: US 7,052,686 B2
(45) Date of Patent: May 30, 2006

(54) PEGYLATED INTERLEUKIN-10

(75) Inventors: Seoju Lee, Edison, NJ (US); David C. Wylie, Cranford, NJ (US); Susan V. Cannon-Carlson, Wayne, NJ (US)

(73) Assignee: Schering Corporation, Kenilworth, NJ (US)

( * ) Notice: Subject to any disclaimer, the term of this patent is extended or adjusted under 35 U.S.C. 154(b) by 179 days.

(21) Appl. No.: 09/967,223

(22) Filed: Sep. 28, 2001

(65) Prior Publication Data

US 2002/0044921 A1    Apr. 18, 2002

Related U.S. Application Data

(60) Provisional application No. 60/236,596, filed on Sep. 29, 2000.

(51) Int. Cl.
*A61K 38/20* (2006.01)
*C07K 14/54* (2006.01)
*A61P 29/00* (2006.01)

(52) U.S. Cl. .................. 424/85.2; 435/69.52; 530/351; 530/345; 530/402; 530/406; 424/78.3; 424/78.38; 514/2; 514/12; 525/54.1

(58) Field of Classification Search ............... 424/78.3, 424/85.2, 78.38; 525/54.1; 530/351, 345, 530/402, 406; 514/2, 12; 435/69.52
See application file for complete search history.

(56) References Cited

U.S. PATENT DOCUMENTS

| | | | |
|---|---|---|---|
| 5,252,714 A | 10/1993 | Harris et al. | |
| 5,643,575 A | 7/1997 | Martinez et al. | |
| 5,824,784 A | 10/1998 | Kinstler | |
| 5,908,621 A | 6/1999 | Glue et al. | |
| 5,919,455 A | 7/1999 | Greenwald et al. | |
| 5,932,462 A | 8/1999 | Harris et al. | |
| 5,951,974 A | 9/1999 | Gilbert et al. | |
| 5,985,265 A | 11/1999 | Kinstler et al. | |

| | | | |
|---|---|---|---|
| 6,217,857 B1 | 4/2001 | Mosmann et al. | |
| 2003/0186386 A1* | 10/2003 | Hansen et al. | |

FOREIGN PATENT DOCUMENTS

| | | |
|---|---|---|
| EP | 0 251 304 | 1/1988 |
| WO | WO 9506058 A | 3/1995 |
| WO | WO 9611953 A | 4/1996 |
| WO | WO 9932134 A | 7/1999 |
| WO | WO 0158950 A | 8/2001 |

OTHER PUBLICATIONS

U.S. Appl. No. 60/184,024.*
U.S. Appl. No. 60/230,093.*
Modification of CD4 Immunoadhesin with Monomethoxypoly(ethylene glycol) Aldehyde via Reductive Alkylation, Chamow et al., Bioconjugate Chem. 5, 133-140 (1994).
The conjugation of proteins with polyethylene glycol and other polymers Altering properties of proteins to enhance their therapeutic potential, N.V. Katre, Advanced Drug Delivery Reviews 10:91-114 (1993).
Characterization and Stability of N-terminally PEGylated rhG-CSF, Kinstler et al., Pharm. Res. 13:996-1002 (1996).
Administration of Interleukin-10 at the Time of Priming Protects Corynebacterium parvum-Primed Mice against LPS- and TNF-α-Induced Lethality, Smith et al., Cellular Immunology 173:207-214 (1996).
International Search Report, Patent Cooperation Treaty, International Application No. PCT/US 01/42431, Aug. 9, 2002.

* cited by examiner

*Primary Examiner*—Edward J. Webman

(57) ABSTRACT

Interleukin-10 (IL-10) conjugated via a linker to one or more polyethylene glycol (PEG) molecules at a single amino acid residue of the IL-10, and a method for preparing the same, are provided. The method produces a stable mono-pegylated IL-10, which retains IL-10 activity, where pegylation is selective for the N-terminus on one subunit of IL-10 with little or no formation of monomeric IL-10. The method also provides a substantially homogenous population of mono-PEG-IL-10.

22 Claims, No Drawings

PEGYLATED INTERLEUKIN-10

This application claims priority under 35 U.S.C. § 119(e) to U.S. Provisional Application Ser. No. 60/236,596 filed Sep. 29, 2000, which is hereby incorporated by reference in its entirety.

FIELD OF THE INVENTION

This invention relates to pegylated IL-10 and to methods for preparation of pegylated IL-10, and the like.

BACKGROUND OF THE INVENTION

The cytokine interleukin-10 (IL-10) is a dimer that becomes biologically inactive upon disruption of the non-covalent interactions connecting its two monomer subunits. IL-10 was first identified as a product of the type 2 helper T cell and later shown to be produced by other cell types including B cells and macrophages. It also inhibits the synthesis of several cytokines produced from type 1 helper T cells, such as γ-interferon, IL-2, and tumor necrosis factor-α (TNF-α). The ability of IL-10 to inhibit cell-mediated immune response modulators and suppress antigen-presenting cell-dependent T cell responses demonstrates IL-10 has immunosuppressive properties. This cytokine also inhibits monocyte/macrophage production of other cytokines such as IL-1, IL-6, IL-8, granulocyte-macrophage colony-stimulating factor (GM-CSF), granulocyte colony-stimulating factor (G-CSF), and TNF-α. As a result of its pleiotropic activity, IL-10 is under investigation for numerous clinical applications, such as for treating inflammatory conditions, bacterial sepsis, enterotoxin-induced lethal shock, and autoimmune diseases, e.g., rheumatoid arthritis, allograft rejection and diabetes.

IL-10 has a relatively short serum half-life in the body. For example, the half-life in mice as measured by in vitro bioassay or by efficacy in the septic shock model system [see Smith et al., Cellular Immunology 173:207–214 (1996)] is about 2 to 6 hours. A loss of IL-10 activity may be due to several factors, including renal clearance, proteolytic degradation and monomerization in the blood stream.

Pegylation of a protein can increase its serum half-life by retarding renal clearance, since the PEG moiety adds considerable hydrodynamic radius to the protein. However, the conventional pegylation methodologies are directed to monomeric proteins and larger, disulfide bonded complexes, e.g., monoclonal antibodies. Pegylation of IL-10 presents problems not encountered with other pegylated proteins known in the art, since the IL-10 dimer is held together by non-covalent interactions. Dissociation of IL-10, which may be enhanced during pegylation, will result in pegylated IL-10 monomers (PEG-IL-10 monomers). The PEG-IL-10 monomers do not retain biological activity of IL-10. It is also noted that di-PEG-IL-10, i.e., pegylation on two amino acids residues of IL-10, does not retain significant in vitro biological activity.

It would be an advantage to have an IL-10 product that is better able to tolerate systemic exposure during treatment, by enhancing the circulating life (delayed clearance), solubility and stability of IL-10, without disrupting the dimeric structure and affecting the activity of IL-10. The present invention addresses this and other related needs in the art.

SUMMARY OF THE INVENTION

This invention provides pegylated IL-10 (PEG-IL-10), more particularly mono-PEG-IL-10, methods for making the same, and pharmaceutical compositions containing mono-PEG-IL-10.

In one aspect, the invention is a mono-PEG-IL-10 which contains from one to nine PEG molecules covalently attached via a linker to the alpha amino group of the amino acid residue at the N-terminus (amino terminus) of one subunit of the IL-10. Thus, this mono-PEG-IL-10 of the present invention can be expressed by the formula:

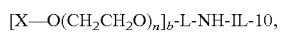

[X—O(CH$_2$CH$_2$O)$_n$]$_b$-L-NH-IL-10, where

L is a linker which comprises a $C_{2-12}$ alkyl;

b represents from 1 to 9 PEG molecules covalently attached to the linker L;

n is from about 20 to 2300 representing the repeating units of each PEG molecule attached to linker L, where n can be the same or different for each PEG molecule, and the sum of the repeating units represented by n for the PEG molecules does not exceed 2300;

X is H or $C_{1-4}$ alkyl; and

N is a nitrogen of the alpha amino group of the amino acid residue at the N-terminus of one subunit of the IL-10 protein, which is covalently attached to the linker L.

Since the sum of n for all PEG molecules does not exceed 2300, the total molecular mass of the PEG molecules attached to the linker does not exceed about 100,000 Da.

In a specific embodiment, the linker L of a PEG-IL-10 contains a propyl group (e.g., —CH$_2$CH$_2$CH$_2$—), which is attached at the amino terminus of the IL-10.

In another aspect, the invention provides pharmaceutical compositions containing stable mono-PEG-IL-10.

This invention further provides PEG-IL-10 compositions, where at least 80% of the PEG-IL-10 is stable mono-PEG-IL-10. The present invention also provides PEG-IL-10 compositions, where the population of mono-PEG-IL-10 is at least 80% positional isomer of mono-PEG-IL-10 which is pegylated on the N-terminus of one subunit of IL-10.

In yet another aspect, this invention relates to a process for preparing PEG-IL-10, more particularly mono-PEG-IL-10, by reacting IL-10 with an activated PEG-aldehyde linker in the presence of a reducing agent to produce a PEG-IL-10. This process minimizes disruption of the dimeric structure of IL-10, such that there is little or no formation of monomeric proteins.

In a particular embodiment of a method of the present invention, a process for preparing a PEG-IL-10 includes reacting IL-10 with an activated PEG-aldehyde linker in the presence of a sodium cyanoborohydride where the molar ratio of IL-10 to sodium cyanoborohydride is from about 1:5 to about 1:15 to form a PEG-IL-10 at a pH of about 6.3 to about 7.5 at a temperature of 18° C. to 25° C., such that the linker is covalently attached to one amino acid residue of the IL-10.

These and other aspects of the invention are explained in greater detail in the following detailed description of the invention.

DETAILED DESCRIPTION OF THE INVENTION

All publications cited herein are expressly incorporated by reference in their entireties.

This invention provides pegylated IL-10 (also referred to herein as "PEG-IL-10"). Preferably, a PEG-IL-10 of this invention contains one or more polyethylene glycol (EG) molecules covalently attached to only one ("mono") amino acid residue of the IL-10 protein via a linker, such that the attachment of the PEG is stable. Thus, the pegylation occurs on a single amino acid residue of IL-10 to provide mono-PEG-IL-10.

More than one PEG molecule can be attached to the single amino acid residue via a linker that is capable of accommodating more than one PEG molecule. A linker (for covalent attachment to IL-10) used in this invention preferably contains an aldehyde group, which chemically reacts with an amino or imino group of an amino acid residue, e.g., the alpha amino group at the N-terminus of the polypeptide, the epsilon amino group of lysine or an imino group of histidine. In order to obtain a stable mono-PEG-IL-10 it is preferred that a PEG is attached at the amino terminus or to a lysine residue of IL-10 versus a histidine residue. Most preferably, a mono-PEG-IL-10 of this invention contains one or more PEG molecules covalently attached via a linker to the alpha amino group of the N-terminus of only one subunit of IL-10. It is noted that an IL-10 containing a PEG molecule is also known as a conjugated protein, whereas the protein lacking an attached PEG molecule can be referred to as unconjugated.

Reaction conditions for pegylation are selected to minimize disruption of the dimeric structure of IL-10. Thus, production of pegylated IL-10 monomers, which lack IL-10 activity, is reduced by a method of the invention, described infra. Preferably, the reaction conditions used in a method of the invention permit selective pegylation on the alpha amino group of the N-terminus of IL-10 (N-terminal-PEG-IL-10) to minimize production of other PEG-IL-10 positional isomers, e.g., His-PEG-IL-10 and Lys-PEG-IL-10. It is desirable, and advantageous, to have a single positional isomer of a therapeutic drug product for numerous reasons, including regulatory approval, consistent properties to allow better analytical characterization of the product in vivo and greater consistency and control of the process for making it.

A method of the present invention provides compositions containing a population of stable mono-PEG-IL-10, i.e., the PEG moiety of a mono-PEG-IL-10 is not hydrolyzed from the pegylated amino acid residue using a hydroxylamine assay, e.g., 450 mM hydroxylamine (pH 6.5) over 8 to 16 hours at room temperature. Thus, populations of stable mono-PEG-IL-10 (described supra) can be achieved in PEG-IL-10 compositions, where greater than 80% of the composition is stable mono-PEG-IL-10, more preferably at least 90%, and most preferably at least 95%. However, greater than 98% mono-PEG-IL-10 can be achieved in a PEG-IL-10 composition, as shown in the Example infra. Furthermore, a method of the present invention provides PEG-IL-10 compositions containing a substantially homogeneous population of mono-PEG-IL-10, where at least 80%, more preferably at least 90%, of the mono-PEG-IL-10 is a positional isomer which is pegylated at the N-terminus of IL-10.

Interleukin-10

General methods of molecular biology are described in, e.g., Sambrook et al., *Molecular Cloning: A Laboratory Manual*, Cold Spring Harbor Laboratory Press, Cold Spring Harbor, N.Y. 2d ed. (1989); and Brent, et al. *Current Protocols in Molecular Biology*, John Wiley & Sons, Inc., New York, Ausubel et al., eds. (1988 and periodic supplements).

An "interleukin-10" or "IL-10" protein used in this invention, whether conjugated to a polyethylene glycol, i.e., PEG-IL-10, or in a non-conjugated form, is a protein comprising two subunits (monomers) joined by non-covalent interactions to form a dimer. The terms "monomeric IL-10" and "IL-10 monomer" refer to one subunit of IL-10, which does not possess biological activity of native IL-10. Thus, an IL-10 used in this invention to make PEG-IL-10 is a dimer which possesses activity of native IL-10.

An IL-10 protein used in the present invention contains an amino acid sequence that shares an observed homology of at least 75%, more preferably at least 85%, and most preferably at least 90% or more, e.g., at least 95%, with the sequence of a mature IL-10 protein, i.e., lacking any leader sequences. See, e.g., U.S. Pat. No. 6,217,857. Amino acid sequence homology, or sequence identity, is determined by optimizing residue matches and, if necessary, by introducing gaps as required. Homologous amino acid sequences are typically intended to include natural allelic, polymorphic and interspecies variations in each respective sequence. Typical homologous proteins or peptides will have from 25–100% homology (if gaps can be introduced) to 50–100% homology (if conservative substitutions are included) with the amino acid sequence of the IL-10 polypeptide. See Needleham et al., J. Mol. Biol. 48:443–453 (1970); Sankoff et al. in *Time Warps, String Edits, and Macromolecules: The Theory and Practice of Sequence Comparison*, 1983, Addison-Wesley, Reading, Mass.; and software packages from IntelliGenetics, Mountain View, Calif., and the University of Wisconsin Genetics Computer Group, Madison, Wis.

The IL-10 can be glycosylated or unglycosylated. Muteins or other analogs, including the BCRF1 (Epstein Barr Virus viral IL-10) protein, can also be used. Modifications of sequences encoding IL-10 can be made using a variety of techniques, e.g., site-directed mutagenesis [Gillman et al., Gene 8:81–97 (1979); Roberts et al., Nature 328:731–734 (1987)], and can be evaluated by routine screening in a suitable assay for IL-10 activity. Modified IL-10 proteins, e.g., variants, can vary from the naturally-occurring sequence at the-primary structure level. Such modifications can be made by amino acid insertions, substitutions, deletions and fusions. IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although others may be post-translational variants, e.g., glycosylated variants. Any variant of IL-10 can be used in this invention provided it retains a suitable level of IL-10 activity.

IL-10 used in this invention can be derived from a mammal, e.g. human or mouse. Human IL-10 (hIL-10) is preferred for treatment of humans in need of IL-10 treatment. IL-10 used in this invention is preferably a recombinant IL-10.

Methods describing the preparation of human and mouse IL-10 can be found in U.S. Pat. No. 5,231,012. In another embodiment of the present invention, IL-10 can be of viral origin. The cloning and expression of a viral IL-10 from Epstein Barr virus (BCRF1 protein) is disclosed in Moore et al., Science 248:1230 (1990).

IL-10 can be obtained in a number of ways using standard techniques known in the art, e.g., isolated and purified from culture media of activated cells capable of secreting the protein (e.g., T-cells), chemically synthesized, or recombinant techniques, (see, e.g., Merrifield, Science 233:341–47 (1986); Atherton et al., *Solid Phase Peptide Synthesis, A Practical Approach*, 1989, I.R.L. Press, Oxford; U.S. Pat. No. 5,231,012 which teaches methods for the production of proteins having IL-10 activity, including recombinant and other synthetic techniques). Preferably, IL-10 protein is obtained from nucleic acids encoding the IL-10 polypeptide using recombinant techniques. Recombinant human IL-10 is also commercially available, e.g., from PeproTech, Inc., Rocky Hill, N.J.

IL-10 exhibits several biological activities, which could form the basis of assays and units. See, e.g., *Current Protocols in Immunology*, John Wiley & Sons, NY Coligan et al., eds., (1991 and periodic supplements). IL-10 activity is described in, e.g., U.S. Pat. No. 5,231,012 and in International Patent Publication No. WO 97/42324, which provide in vitro assays suitable for measuring such activity. In particular, IL-10 inhibits the synthesis of at least one cytokine in the group consisting of IFN-γ, lymphotoxin, IL-2, IL-3, and GM-CSF in a population of T helper cells induced to synthesize one or more of these cytokines by exposure to antigen and antigen presenting cells (APCs). IL-10 also has the property of stimulating cell growth, and by measuring cell proliferation after exposure to the cytokine, IL-10 activity can be determined.

As already described above, the activity of a mono-PEG-IL-10 of the present invention can be determined using a standard IL-10 activity assay known in the art. Preferably, mono-PEG-IL-10 retains at least 5% activity of the unconjugated IL-10. Activity greater than 30% is attainable from a mono-PEG-IL-10 of this invention, as demonstrated in Example 1. Preferably, a mono-PEG-IL-10 of the invention has significantly increased bioavailability in the body of a patient compared with the unconjugated IL-10, e.g., as shown by Example 2.

Polyethylene Glycol

It shall be appreciated by those having ordinary skill in the art that various polymers can be used in addition to PEG for attachment at the N-terminus of one monomer of IL-10, such as polyoxyethylene 2-methyl-2-propenyl methyl diether, or polyoxyethylene allylmethyldiether, however PEG is most preferred. Thus, by way of example, PEG is used to describe this invention.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138–161). The term "PEG" is used broadly to encompass any polyethylene glycol molecule, without regard to size or to modification at an end of the PEG, and can be represented by the formula:

$$X\text{—}O(CH_2CH_2O)_{n-1}CH_2CH_2OH, \tag{1}$$

where n is 20 to 2300 and X is H or a terminal modification, e.g., a $C_{1-4}$ alkyl.

Preferably, a PEG used in the invention terminates on one end with hydroxy or methoxy, i.e., X is H or $CH_3$ ("methoxy PEG"). It is noted that the other end of the PEG, which is shown in formula (1) terminating in OH, covalently attaches to a linker moiety via an ether oxygen bond.

When used in a chemical structure, the term "PEG" includes the formula (1) above without the hydrogen of the hydroxyl group shown, leaving the oxygen available to react with a free carbon atom of a linker of the invention to form an ether bond.

Any molecular mass for a PEG can be used as practically desired, e.g., from about 1,000 Daltons (Da) to 100,000 Da (n is 20 to 2300). The number of repeating units "n" in the PEG is approximated for the molecular mass described in Daltons. It is preferred that the combined molecular mass of PEG on an activated linker is suitable for pharmaceutical use. Thus, the combined molecular mass of the PEG molecules should not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270).

Preferably, the combined or total molecular mass of PEG used in a PEG-IL-10 is from about 3,000 Da to 60,000 Da (total n is from 70 to 1,400), more preferably from about 10,000 Da to 36,000 Da (total n is about 230 to about 820). The most preferred combined mass for PEG is from about 12,000 Da to 24,000 Da (total n is about 270 to about 550).

One skilled in the art can select a suitable molecular mass for the PEG, e.g., based on how the pegylated IL-10 will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91–114 (1993).

Activated PEG

To conjugate PEG to IL-10, an activated linker covalently attached to one or more PEG molecules is reacted with an amino or imino group of an amino acid residue, most preferably with an alpha amino group at the N-terminus of IL-10, to form a mono-PEG-IL-10 of the present invention.

A linker is "activated" if it is chemically reactive and ready for covalent attachment to an amino group on an amino acid residue. Any activated linker can be used in this invention provided it can accommodate one or more PEG molecules and form a covalent bond with an amino group of an amino acid residue under suitable reaction conditions. Preferably, the activated linker attaches to an alpha amino group in a highly selective manner over other attachment sites, e.g., epsilon amino group of lysine or imino group of histidine.

Activated PEG can be represented by the formula:

$$(PEG)_b\text{-}L', \tag{2}$$

where PEG (defined supra) covalently attaches to a carbon atom of the linker to form an ether bond, b is 1 to 9 (i.e. 1 to 9 PEG molecules can be attached to the linker), and L' contains a reactive group (an activated moiety) which can react with an amino or imino group on an amino acid residue to provide a covalent attachment of the PEG to IL-10.

A preferred activated linker (L') of the invention contains an aldehyde of the formula RCHO, where R is a linear (straight chain) or branched $C_{1-11}$ alkyl. After covalent attachment of an activated linker to IL-10, the linker (referred to as "-L-" in the structural formulas recited herein) between the IL-10 and PEG contains 2 to 12 carbon atoms.

Propionaldehyde is an example of a preferred activated linker of this invention. PEG-propionaldehyde, represented in formula (3), is described in U.S. Pat. No. 5,252,714 and is commercially available from Shearwater Polymers (Huntsville, Ala).

$$PEG\text{-}CH_2CH_2CHO \quad (3)$$

If it is desirable to covalently attach more than one PEG molecule to IL-10, then a suitable activated branched (also known as "multi-armed") linker can be used. Any suitable branched PEG linker that covalently attaches two or more PEG molecules to an amino group on an amino acid residue of IL-10, more preferably to an alpha amino group at the N-terminus, can be used. Preferably, a branched linker used in this invention contains two or three PEG molecules.

For example, a branched PEG linker used in this invention can be a linear or branched aliphatic group that is hydrolytically stable and contains an activated moiety, e.g., an aldehyde group, which reacts with an amino group of an amino acid residue, as described above. Preferably, the aliphatic group of a branched linker contains 2 to 12 carbons. For example, an aliphatic group can be a t-butyl which contains as many as three PEG molecules on each of three carbon atoms (i.e., a total of 9 PEG molecules) and a reactive aldehyde moiety on the fourth carbon of the t-butyl.

Examples of activated, branched PEG linkers are also described in U.S. Pat. Nos. 5,643,575, 5,919,455, and 5,932,462. One having ordinary skill in the art can prepare modifications to branched PEG linkers as desired, e.g., addition of a reactive aldehyde moiety.

Methods for the preparation of linkers for use in the present invention are well known in the art, e.g., see U.S. Pat. Nos. 5,643,575, 5,919,455, and 5,932,462. Activated PEG-linkers, such as PEG-aldehydes, can be obtained from a commercial source, e.g., Shearwater Polymers, (Huntsville, Ala.) or Enzon, Inc. (Piscataway, N.J.).

Pegylated IL-10

A mono-PEG-IL-10 of this invention is an IL-10 that has a linker containing one or more PEG molecules, which is covalently attached to only one amino acid residue of the IL-10. Preferred mono-PEG-IL-10 molecules of the invention contain a PEG-linker attached to an amino acid residue of IL-10 to form a hydrolytically stable bond, e.g. on the alpha amino group at the N-terminus or on the side chain of a lysine residue. (The stability of a mono-PEG-IL-10 protein of the invention can be determined by a conventional hydroxylamine assay, e.g., using conditions as described above.) Most preferably, the PEG is attached at the N-terminus of an IL-10 subunit on the nitrogen atom of the alpha amino group. Thus, over an entire IL-10 protein containing two subunits, only one subunit is pegylated on one amino acid residue.

A preferred mono-PEG-IL-10 of the invention is represented by the structural formula:

$$(PEG)_b\text{-}L\text{-}NH\text{-}IL\text{-}10 \quad (4)$$

where PEG, b, and L (linker) are as described, and N is nitrogen of an amino or imino group of an amino acid residue on one subunit of IL-10. If b is greater than one, then L must be a suitable linker which attaches two or more PEG molecules to an amino acid residue of IL-10.

For example, if the linker is a PEG-propionaldehyde and b is 1 then upon covalent attachment of the linker to an amino acid residue of the IL-10, the PEG-IL-10 can have a structural formula (5) as shown:

$$PEG\text{-}CH_2CH_2CH_2\text{—}NH\text{-}IL\text{-}10. \quad (5)$$

Conjugation Reaction Between PEG and IL-10

Although not intending to limit the scope of the invention to any one theory, the following schematic illustrates a reaction between an activated PEG aldehyde linker and an amino or imino group of an amino acid residue of one of the IL-10 monomers:

$$PEG\text{-}R\text{—}CHO+NH_2\text{-}IL\text{-}10 \rightleftharpoons PEG\text{-}R\text{—}CH\text{=}N\text{-}IL\text{-}10 \quad (6)$$

where R is a $C_{1-11}$ alkyl and N is nitrogen of a reactive amino group on an amino acid residue of IL-10. In reaction (6), the activated PEG covalently attaches to the IL-10 to form an imine linkage. Reduction of the imine linkage by the reducing agent, e.g., sodium cyanoborohydride (Sigma-Aldrich, St. Louis, Mo.) forms pegylated IL-10, as shown:

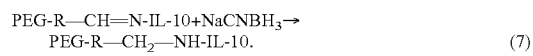

$$PEG\text{-}R\text{—}CH\text{=}N\text{-}IL\text{-}10+NaCNBH_3 \rightarrow$$
$$PEG\text{-}R\text{—}CH_2\text{—}NH\text{-}IL\text{-}10. \quad (7)$$

Other reducing agents can be used instead of sodium cyanoborohydride in this reaction, including sodium borohydride, tertiary butyl amine borane, sodium triacetyl borohydide, dimethylamine borate, trimethylamine borate, and pyridine borate. Sodium cyanoborohydride is preferred because it specifically reduces an imine linkage, which is formed between an aldehyde group of the activated PEG and amino group of the amino acid of IL-10.

As shown in reactions (6) and (7), a Schiff base is formed during the preparation of mono-PEG-IL-10. There was concern that this intermediate, which is very difficult to separate from mono-PEG-IL-10, could lower the purity of the mono-PEG-IL-10 if the intermediate accumulates in the reaction and is not reduced to the product. Typically, this problem is avoided by using higher concentrations of reducing agent, e.g., see Kinstler et al., Pharm. Res. 13:996–1002 (1996) and Chamow et al., Bioconjugate Chem. 5: 133–140 (1994). However, there was farther concern that the higher concentrations of reducing agent, e.g., sodium cyanoborohydride, used conventionally would disrupt the dimeric structure of IL-10. For example, as little as about 14 mM sodium cyanoborohydride can result in more than 10% monomerization of IL-10.

It was discovered during the development of a method of the present invention that reaction (6) is reversible and that equilibrium greatly favors the hydrolysis of the Schiff base (i.e., the imine) reaction intermediate. It is believed that the intermediate is very unstable and is quickly hydrolyzed in the absence of reducing agent. This was demonstrated by incubating activated PEG linker with IL-10 in the absence of a reducing agent. No pegylated IL-10 (unreduced or reduced) was detectable by size exclusion (SE)-HPLC after 24 hours, however the addition of sodium cyanoborohydride produced mono-PEG-IL-10 of the invention instantly. Based on these results, much lower concentrations of a reducing agent are used to prepare PEG-IL-10 of the present invention in comparison with concentrations of reducing agent taught in the art. This is an advantage over conventional methods of pegylating proteins because although a low concentration of reducing agent is employed the purity of the mono-IL-10 product is not reduced, i.e., no intermediate is present, and IL-10 monomerization is controlled.

The ratio of IL-10 to the reducing agent can be from about 1:0.5 to 1:50, more preferably from about 1:1 to 1:30. Most preferably, the molar ratio of IL-10 to the reducing agent is from about 1:5 to 1:15 to minimize any disruption of the IL-10 during pegylation. Incubating molar ratios of less than 10:1 of sodium cyanoborohydride to IL-10 in a method of the present invention does not disrupt the dimeric structure of IL-10. The ability to use lesser amounts of reducing agent to reduce the Schiff base into a secondary amine, thereby accomplishing pegylation, was surprising in light of the teachings in the art, i.e., significantly higher molar ratios of sodium cyanoborohydride to protein is necessary to pegylate proteins (e.g., about 75:1 to 350:1; see, e.g., Kinstler et al., supra and Chamow et al., supra).

In a method of the present invention, the molar ratio of the activated PEG linker to IL-10 can be from about 0.5:1 to 20:1, more preferably 2:1 to 8:1.

Various aqueous buffers can be used in the present method to catalyze the covalent addition of PEG to IL-10. The pH of a buffer used is from about 5.5 to 7.8, more preferably the pH is in a neutral range, e.g., from about 6.3 to 7.5. In order not to disrupt the non-covalent interactions between the two subunits of IL-10, it is desirable to maintain IL-10 in this neutral pH range, in particular, during the pegylation reaction. This neutral pH range also increases the site-specific pegylation of IL-10 at the alpha amino group of the N-terminus versus other imino or amino groups of other amino acid residues, e.g., lysine or histidine. Buffers having a pKa close to neutral pH range are preferred, e.g., phosphate buffer. Preferably, buffers and pH are selected that do not result in monomerization of IL-10. IL-10 monomerization can be detected and monitored using conventional SE-IPLC.

The temperature range for preparing a mono-PEG-IL-10 of the invention is from about 5° C. to 30° C. More preferably, the temperature is from about 18° C. to 25° C.

The pegylation reaction can proceed from 3 to 48 hours, more preferably 10 to 24 hours. The reaction can be monitored using SE-HPLC, which can distinguish IL-10, mono-PEG-IL-10 and di-PEG-IL-10 (i.e., pegylation occurs on two amino acid residues of IL-10, typically on both subunits). It is noted that mono-PEG-IL-10 forms before di-PEG-IL-10. When the mono-PEG-IL-10 concentration reaches a plateau, the reaction can be terminated by adding glycine solution to quench any remaining activated PEG. Using reaction conditions according to a method of the invention, typically 5 to 10% di-PEG-IL-10 and 38% to 43% mono-PEG-IL-10 is formed (the remainder being unmodified IL-10).

Conventional separation and purification techniques known in the art can be used to purify mono-PEG-IL-10, such as size exclusion (e.g. gel filtration) and ion exchange chromatography, which can separate pegylated IL-10 monomers and di-PEG-IL-10 from the mono-PEG-IL-10 of the invention.

It may be desirable to polish or resolve a population of mono-PEG-IL-10 in a PEG-IL-10 composition prepared according to a method of the present invention. The polishing step separates less stable mono-PEG-IL-10 (e.g. His-PEG-IL-10) from stable mono-PEG-IL-10 (e.g. N-terminus-PEG-IL-10 or Lys-PEG-IL-10), and thus can achieve greater homogeneity of stable positional isomers, e.g., greater than 95% of a PEG-IL-10 composition. Less stable positional isomers of PEG-IL-10, e.g., histidine-PEG-IL-10, can be hydrolyzed during a polishing step. The population of PEG-IL-10 can be incubated in an aqueous buffer, preferably a TRIS buffer (e.g., 10 to 300 mM, more preferably about 30 to 70 mM), at about pH 5.0 to 9.0, more preferably pH 7.0 to 8.0 at 15° C. to 35° C. overnight. Alternatively, the population of PEG-IL-10 can be treated with 0.05 to 0.4 M hydroxylamine HCl salt (pH about 6.5) at room temperature for 0.5 to 10 hours. Hydrolyzed IL-10 and PEG remnant can be removed from the population of stable mono-PEG-IL-10 by a separation/purification step using, e.g., gel filtration or ion exchange chromatography.

In U.S. Pat. No. 5,985,265 the pegylation of interferon using an aldehyde linker was accomplished at acidic pH 4.0 at 4° C. Pegylation of IL-10 at this pH would result in its monomerization and loss of biological activity. Conventional wisdom in the art teaches that for most activated PEG, as the reaction pH is increased under basic conditions pegylation occurs at more stable sites on the protein. For example, succinimidyl carbonate-PEG forms about 90% Lys-PEG-IL-10 (more stable) and about 10% His-PEG-IL-10 (less stable) at a reaction pH 8.8, and about 64% Lys-PEG-IL-10 and 36% His-PEG-IL-10 at a reaction pH 6.3. However, during the discovery of the present invention, it was determined that as the pH of a pegylation reaction using an aldehyde linker is increased above a neutral pH range, pegylation occurs more frequently at less stable sites of IL-10, e.g., His-PEG-IL-10, thereby forming a heterogenous mixture of unstable PEG-IL-10. Thus, it was unexpected that IL-10 pegylation using an aldehyde linker in neutral pH range would provide a highly stable and homogeneous population of pegylated IL-10.

Pharmaceutical Compositions Containing PEG-IL-10

A PEG-IL-10 of this invention is useful in the treatment of conditions which are treatable with IL-10, e.g., diseases associated with undesired T-cell activation and T-cell expansion such as autoimmune diseases, organ and bone marrow transplant rejection, graft-versus-host disease, parasitic infections, granulomas, inflammatory diseases, Crohn's disease, colitis, pancreatitis, inflammatory lung, eye diseases, allergic conditions, asthma, atopic dermatitis, and rhinitis.

PEG-IL-10 can be formulated in a pharmaceutical composition comprising a therapeutically effective amount of the IL-10 and a pharmaceutical carrier. A "therapeutically effective amount" is an amount sufficient to provide the desired therapeutic result. Preferably, such amount has minimal negative side effects. The amount of PEG-IL-10 administered to treat a condition treatable with IL-10 is based on IL-10 activity of the conjugated protein, which can be determined by IL-10 activity assays known in the art. The therapeutically effective amount for a particular patient in need of such treatment can be determined by considering various factors, such as the condition treated, the overall health of the patient, method of administration, the severity of side-effects, and the like.

The therapeutically effective amount of pegylated IL-10 can range from about 0.01 to about 100 µg protein per kg of body weight per day. Preferably, the amount of pegylated IL-10 ranges from about 0.1 to 20 µg protein per kg of body weight per day, more preferably from about 0.5 to 10 µg protein per kg of body weight per day, and most preferably from about 1 to 4 µg protein per kg of body weight per day. Less frequent administration schedules can be employed using the PEG-IL-10 of the invention since this conjugated form is longer acting than IL-10. The pegylated IL-10 is formulated in purified form and substantially free of aggregates and other proteins. Preferably, IL-10 is administered by continuous infusion so that an amount in the range of about 50 to 800 μg protein is delivered per day (i.e., about 1 to 16 μg protein per kg of body weight per day PEG-IL-10). The daily infusion rate may be varied based on monitoring of side effects and blood cell counts.

To prepare pharmaceutical compositions containing mono-PEG-IL-10, a therapeutically effective amount of PEG-IL-10 is admixed with a pharmaceutically acceptable carrier or excipient. Preferably the carrier or excipient is inert. A pharmaceutical carrier can be any compatible, non-toxic substance suitable for delivering the IL-10 compositions of the invention to a patient. Examples of suitable carriers include normal saline, Ringer's solution, dextrose solution, and Hank's solution. Non-aqueous carriers such as fixed oils and ethyl oleate may also be used. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives.

Compositions of the invention can be administered orally or injected into the body. Formulations for oral use can also include compounds to further protect the IL-10 from proteases in the gastrointestinal tract. Injections are usually intramuscular, subcutaneous, intradermal or intravenous. Alternatively, intra-articular injection or other routes could be used in appropriate circumstances. When administered parenterally, pegylated IL-10 is preferably formulated in a unit dosage injectable form (solution, suspension, emulsion) in association with a pharmaceutical carrier. See, e.g., Avis et al., eds., *Pharmaceutical Dosage Forms: Parenteral Medications*, Dekker, N.Y. (1993); Lieberman et al., eds., *Pharmaceutical Dosage Forms: Tablets*, Dekker, N.Y. (1990); and Lieberman et al., eds., *Pharmaceutical Dosage Forms: Disperse Systems*, Dekker, N.Y. (1990). Alternatively, compositions of the invention may be introduced into a patient's body by implantable or injectable drug delivery system, e.g., Urquhart et al. *Ann. Rev. Pharmacol. Toxicol.* 24:199–236, (1984); Lewis, ed., *Controlled Release of Pesticides and Pharmaceuticals* Plenum Press, New York (1981); U.S. Pat. Nos. 3,773,919; 3,270,960; and the like. The pegylated IL-10 can be administered in aqueous vehicles such as water, saline or buffered vehicles with or without various additives and/or diluting agents.

Preparation of such pharmaceutical compositions is known in the art; see, e.g., *Remington's Pharmaceutical Sciences and U.S. Pharmacopeia: National Formulary*, Mack Publishing Company, Easton, Pa. (1984).

EXAMPLE 1

In this Example human IL-10 (hIL-10) was used, however, other forms of IL-10, e.g., mouse, viral or an IL-10 variant, can be used without affecting the pegylation reaction.

The conjugation reaction was performed at pH 6.3 in an attempt to maximize the probability of site-specific pegylation at the N-terminus of one subunit of IL-10 without disrupting the IL-10 structure. The molar ratio of IL-10 to reducing agent (sodium cyanoborohydride; Sigma-Aldrich, St. Louis, Mo.) was 1:4.5, which is much less than the molar ratios of protein to reducing agent taught in the art, e.g., 1:75 to 1:350 (see Kinstler et al., supra and Chamow et al., supra). Size exclusion-HPLC showed less than 1% of the IL-10 was monomeric by the end of the reaction.

In an attempt to determine the effect of reducing agent concentration on IL-10 stability, i.e., IL-10 dissociation into its subunits, 0.1 mM IL-10 was incubated with varying concentrations of sodium cyanoborohydride (none, 0.5, 1.0, 2.5, 5.0 and 14 mM) at pH 6.3 for 15 hours to determine whether monomerization of IL-10 is a function of the ratio of protein to reducing agent (1:5, 1:10, 1:25, 1:50 and 1:140). The results showed that at higher ratios of reducing agent to protein there were greater levels of IL-10 monomer formed. Surprisingly, at a molar ratio of less than 1:10 of IL-10 to reducing agent, disruption of the dimeric structure of hIL-10 was negligible.

As a result of this discovery, the pegylation reaction was modified accordingly. Purified hIL-10 was dialyzed against different reaction buffers at pH 6.3 and 8.6 (50 mM sodium phosphate, 100 mM sodium chloride, pH 6.3; or 50 mM sodium phosphate, 10 mM sodium tetraborohydrate, 100 mM sodium chloride, pH 8.6). The IL-10 was diluted to 4 mg/ml (0.1 mM in each buffer). Two activated PEG molecules, methoxy-PEG-aldehyde MW 5000 and MW 12000 (Shearwater), were added to each reaction buffer in approximately a 1:1 molar ratio of IL-10 to PEG (in separate studies). Aqueous sodium cyanoborohydride was added to the reaction mixture to a final concentration of 0.5 to 0.75 mM (about 1:4.5 to 1:6.8 IL-10 to reducing agent). The pegylation reaction was carried out at room temperature (18 to 25° C.) for 15 to 20 hours until the desired degree of mono-pegylation, i.e., covalent addition of PEG to one subunit of IL-10, was achieved. The reaction was quenched with glycine. The final reaction solution was analyzed by SE-HPLC to determine the percentage of mono-PEG-IL-10 based on concentrations of hIL-10, mono-PEG-IL-10 and di-PEG-IL-10 and by reverse phase (rp)-HPLC to determine levels of positional isomers. The mono-PEG-IL-10 was then purified from unreacted hIL-10, activated PEG-linker and di-PEG-IL10 by gel filtration chromatography and characterized by rp-HPLC and bioassay (e.g., stimulation of proliferation of BaMR29α1 cells, which is a murine B-cell line created by transfecting Ba/F3 cells with the murine IL-10 receptor cDNA).

Three purified (SE-HPLC) mono-PEG-IL-10 samples contained greater than 98% mono-PEG-IL-10. Contrary to expectations (i.e. pegylation rates of proteins generally occur at higher pH to form a more stable pegylated protein), the rate of formation of stable mono-PEG-IL-10 (where pegylation occurs at the alpha amino group or on lysine) was higher at pH 6.3 than at pH 8.6. Most importantly, SE-HPLC showed no increase in IL-10 monomer at either pH.

Reverse phase HPLC analysis of the final reaction mixtures showed mainly a single positional isomer demonstrating increased selectivity for N-terminal pegylation at pH 6.3, while multiple peaks representing different positional isomers of mono-PEG-IL-10 were observed under higher pH (8.6) conditions. N-terminal amino acid sequencing of the mono-PEG-IL-10 purified from the pH 6.3 reaction mixture indicated that over 40% of PEG-IL-10 was N-terminally blocked. Unlike the hydroxylamine assay, amino acid sequencing measures blockage per monomer. The maximum possible blockage for N-terminally pegylated dimers that are pegylated at a stoichiometry of one PEG-linker per dimer is 50%. Therefore, less than 20% of this preparation was pegylated at sites other than the N-terminus of IL-10 according to sequence analysis, i.e., greater than 80% pegylation at the N-terminus. However, according to rp-HPLC at least 90% of the IL-10 was pegylated at the N-terminus. Moreover, at least 95% of the pegylated IL-10 was stable according to the hydroxylamine assay. The purified mono-PEG- IL-10 was also biologically active, demonstrating about 32% of the specific biological activity of unmodified hIL-10.

Thus, IL-10 was successfully pegylated at the amino terminus using two PEG-aldehyde linker molecules having different molecular weight PEG molecules in a site-specific manner using concentrations of reducing agent below conventional levels. Structurally intact mono-PEG-IL-10 can be formed in high yield as a homogenous population, i.e., a substantially single positional isomer, using this method.

EXAMPLE 2

Previous studies showed the ability of recombinant human IL-10 to suppress the production of pro-inflammatory cytokines in LPS-primed mice (with *C. parvum*) given a lethal dose of lipopolysaccharide (LPS). The primed mice produce high levels of TNF-α and IFN-γ, which are major cytokine mediators of LPS lethality. Recombinant human IL-10 was most effective in suppressing the production of cytokines when administered to *C. parvum* mice simultaneously or one hour at most prior to LPS exposure.

In this Example the *C. parvum*-mouse model was used to compare the duration and extent of suppressive effect of two mono-PEG-IL-10 proteins on cytokine responses triggered by LPS. It demonstrates that a mono-PEG-IL-10 of the present invention maintains biological activity in vivo and has a reduced serum clearance compared with unmodified IL-10.

BDF-1 mice were challenged with LPS, one week after priming with *C. parvum*, according to the method of Smith et al., supra. Mice were bled 1.5 hours after the challenge to determine the levels of circulating TNF-α and 3 hours after challenge to measure circulating levels of IL-12, IL-6 and IFN-γ. IFN-γ and IL-12 responses were inhibited to the same extent by IL-10, and thus IFN-γ data is not shown.

Two different PEG propionaldehydes (PALD) which contain 12,000 or 20,000 Da PEG were used in this study. The mono-PEG-IL-10 proteins were administered subcutaneously ($8 \times 10^5$ units) to mice 20, 48 or 72 hours before the LPS challenge, and also administered to mice simultaneously with LPS to show an initial level of IL-10 activity that could be followed over time. The amount of protein administered to the mice was equalized for each pegylated IL-10 based on specific activity, which was determined using an in vitro bioassay. Control mice were given mouse serum albumin as an inert protein preparation.

The data in the Table below show that PEG-IL-10 inhibits expression of pro-inflammatory cytokines in vivo when administered 48 hours (for PEG-12K) and 72 hours (for PEG-20K) before the LPS challenge. In contrast, native IL-10 was efficacious only when co-administered with LPS. This is likely due to a serum half-life of less than 5 hours for native IL-10, as shown previously in pharmacokinetic (PK) studies. The data from this Example demonstrate that mono-PEG-IL-10 does not lead to rapid monomerization in vivo, and is thus maintained in the body, i.e., without renal clearance.

TABLE

| IL-10 preparation | 0 hr | −20 hr | −48 hr | −72 hr |
|---|---|---|---|---|
| | TNF-α (% inhibition) | | | |
| Non-pegylated IL-10 (10 µg) | 62 | 7 | 8 | 0 |
| PALD-12K (34 µg) | 69 | 93 | 68 | 17 |
| PALD-20K (73 µg) | 61 | 85 | 96 | 78 |

TABLE-continued

| IL-10 preparation | 0 hr | −20 hr | −48 hr | −72 hr |
|---|---|---|---|---|
| | IL-12p40 (% inhibition) | | | |
| Non-pegylated IL-10 (10 µg) | 88 | 2 | 0 | 8 |
| PALD-12K (34 µg) | 87 | 94 | 53 | 20 |
| PALD-20K (73 µg) | 84 | 92 | 91 | 63 |
| | IL-6 (% inhibition) | | | |
| Non-pegylated IL-10 (10 µg) | 44 | 15 | 9 | 15 |
| PALD-12K (34 µg) | 58 | 73 | 73 | 15 |
| PALD-20K (73 µg) | 29 | 91 | 91 | 82 |

The preceding Examples demonstrate experiments performed to further teach the invention. It shall be appreciated by those skilled in the art that the particular embodiments disclosed in the Examples are for purposes of illustration. Numerous equivalent variations of the methods and compositions described can be employed to achieve a substantially similar result without departing from the spirit of the invention

What is claimed is:

1. A mono-pegylated interleukin-10 (mono-PEG-IL-10) comprising one or more polyethylene glycol (PEG) molecules covalently attached via a linker to a single amino acid residue of a single subunit of IL-10, wherein said amino acid residue is the alpha amino group of the N-terminal amino acid residue or the epsilon amino group of a lysine residue.

2. The mono-PEG-IL-10 of claim 1, wherein one or two PEG molecules are attached via said linker to said single amino acid residue.

3. The mono-PEG-IL-10 of claim 1, wherein said subunit of said IL-10 has the formula:

$(PEG)_b$-L-NH-IL-10 wherein b is 1–9 and L is a $C_{2-12}$ alkyl linker moiety covalently attached to a nitrogen (N) of said single amino acid residue.

4. The mono-PEG-IL-10 of claim 3, wherein b is 1 and L is —$CH_2CH_2CH_2$—.

5. The mono-PEG-IL-10 of claim 1, wherein said PEG molecule is covalently attached via said linker to the nitrogen of the alpha amino group of the N-terminal amino acid residue.

6. The mono-PEG-IL-10 of claim 1, wherein said subunit of said IL-10 has the formula:

$[X—O(CH_2CH_2O)_n]_b$-L-NH-IL-10, wherein X is H or $C_{1-4}$ alkyl, n is 20 to 2300, b is 1 to 9 and L is a $C_{1-11}$ alkyl linker moiety which is covalently attached to the nitrogen (N) of the alpha amino group at the amino terminus of one IL-10 subunit; provided that when b is greater than 1, the total of n does not exceed 2300.

7. The mono-PEG-IL-10 of claim 6, wherein L is —$CH_2CH_2CH_2$—.

8. The mono-PEG-IL-10 according to claim 1, wherein said mono-PEG-IL-10 has greater than 30% of the activity of unconjugated IL-10.

9. A composition of pegylated IL-10 comprising the mono-PEG-IL-10 according to claim 1, wherein the population of mono-PEG-IL-10 is at least 80% of a positional isomer in which the PEG is conjugated to the N-terminal amino acid of one subunit of IL-10.

10. A process for preparing a pharmaceutical composition comprising the no-PEG-IL-10 according to claim 1, comprising mixing the mono-PEG-IL-10 with a pharmaceutically acceptable carrier.

11. The mono-PEG-IL-10 according to claim 1, wherein the IL-10 is human IL-10.

12. A pharmaceutical composition comprising the mono-PEG-IL-10 according to claim 11 and a pharmaceutical carrier.

13. The mono-PEG-IL-10 according to claim 11, wherein the PEG molecule has a molecular weight of 12,000 or 20,000 daltons.

14. A pharmaceutical composition comprising the mono-PEG-IL-10 according to claim 13 and a pharmaceutical carrier.

15. A pharmaceutical composition comprising the mono-PEG-IL-10 according to claim 1 in combination with a pharmaceutically acceptable carrier.

16. A method of treating inflammation in an individual in need of such treatment, comprising administering to the individual a therapeutically effective amount of the pharmaceutical composition according to claim 15.

17. A process, for preparing the mono-PEG-IL-10 according to claim 1, comprising the step of:
reacting IL-10 with an activated PEG-aldehyde linker in the presence of a reducing agent to form the mono-PEG-IL-10 under conditions in which the linker is covalently attached to one amino acid residue of the IL-10.

18. The process according to claim 17 wherein:
(a) the reducing agent is sodium cyanoborohydride;
(b) the activated PEG-aldehyde linker is PEG-propionaldehyde;
(c) the PEG is a methoxy-PEG;
(d) the linker is multi-armed;
(e) the ratio of IL-10 to the sodium cyanoborohydride is from about 1:0.5 to 1:50;
(f) the total molecular mass of all PEG comprising the PEG-aldehyde linker is from 3,000 daltons to 60,000 daltons; or
(g) the reacting step is performed at a pH of 5.6 to 7.8.

19. The process according to claim 17, wherein the ratio of IL-10 to the sodium cyanoborohydride is 1:5 to 1:15.

20. The process according to claim 17, wherein the total molecular mess of all PEG comprising the PEG-aldehyde linker is from 10,000 daltons to 36,000 daltons.

21. The process according to claim 17, wherein the reacting step is performed at a pH of 6.3 to 7.5.

22. The process according to claim 17, further comprising a step selected from:
incubating the mono-PEG-IL-10 product in a buffer at pH 5.0 to 9.0; or
treating the mono-PEG-IL-10 product with 0.05 to 0.4 M hydroxylamine HCl salt.

* * * * *

UNITED STATES PATENT AND TRADEMARK OFFICE
CERTIFICATE OF CORRECTION

| | |
|---|---|
| PATENT NO. | : 7,052,686 B2 |
| APPLICATION NO. | : 09/967223 |
| DATED | : May 30, 2006 |
| INVENTOR(S) | : Lee, Seoju |

It is certified that error appears in the above-identified patent and that said Letters Patent is hereby corrected as shown below:

Col. 15, Claim should read as follows:

10. A process for preparing a pharmaceutical composition comprising the mono-PEG-IL-10 according to claim 1. comprising mixing the mono-PEG-IL-10 with pharmaceutically acceptable carrier.

Signed and Sealed this

Twenty-second Day of August, 2006

JON W. DUDAS
*Director of the United States Patent and Trademark Office*